United States Patent
Clozel

(10) Patent No.: US 8,268,847 B2
(45) Date of Patent: Sep. 18, 2012

(54) THERAPEUTIC COMPOSITIONS COMPRISING A SPECIFIC ENDOTHELIN RECEPTOR ANTAGONIST AND A PDE5 INHIBITOR

(75) Inventor: Martine Clozel, Binningen (CH)

(73) Assignee: Actelion Pharmaceuticals, Ltd., Allschwil (CH)

( * ) Notice: Subject to any disclaimer, the term of this patent is extended or adjusted under 35 U.S.C. 154(b) by 599 days.

(21) Appl. No.: 12/439,290

(22) PCT Filed: Aug. 28, 2007

(86) PCT No.: PCT/IB2007/053448
§ 371 (c)(1),
(2), (4) Date: Feb. 27, 2009

(87) PCT Pub. No.: WO2008/026156
PCT Pub. Date: Mar. 6, 2008

(65) Prior Publication Data
US 2009/0318459 A1    Dec. 24, 2009

(30) Foreign Application Priority Data

Aug. 29, 2006   (WO) .................. PCT/IB2006/052999
Oct. 19, 2006   (WO) .................. PCT/IB2006/053857

(51) Int. Cl.
*A01N 43/54*   (2006.01)
*A61K 31/505*  (2006.01)
*C07D 401/00*  (2006.01)

(52) U.S. Cl. ..................................... 514/269; 546/274.4
(58) Field of Classification Search .................. 514/269; 546/274.4
See application file for complete search history.

(56) References Cited

U.S. PATENT DOCUMENTS

| | | | |
|---|---|---|---|
| 4,233,294 A | 11/1980 | Maurer et al. | |
| 5,250,534 A | 10/1993 | Bell et al. | |
| 5,292,740 A | 3/1994 | Burri et al. | |
| 5,859,006 A | 1/1999 | Daugan | |
| 7,094,081 B1 | 8/2006 | Bolli et al. | |
| 7,094,781 B2 | 8/2006 | Bolli et al. | |
| 7,285,549 B2 | 10/2007 | Bolli et al. | |
| 2008/0233188 A1 | 9/2008 | Adesuyi et al. | |
| 2010/0022568 A1 | 1/2010 | Clozel et al. | |

FOREIGN PATENT DOCUMENTS

| | | |
|---|---|---|
| AU | 678467 B2 | 5/1997 |
| EP | 0658548 | 6/1995 |
| EP | 0743307 | 11/1996 |
| EP | 0882719 | 12/1998 |
| EP | 0959072 | 11/1999 |
| EP | 1 097 711 | 5/2001 |
| WO | WO 96/16963 | 6/1996 |
| WO | WO 96/19459 | 6/1996 |
| WO | WO 99/24433 | 5/1999 |
| WO | WO 99/64004 | 12/1999 |
| WO | WO 00/27848 | 5/2000 |
| WO | WO 00/42035 | 7/2000 |
| WO | WO 01/17976 | 6/2001 |
| WO | WO 01/46156 | 6/2001 |
| WO | WO 01/81335 | 11/2001 |
| WO | WO 01/81338 | 11/2001 |
| WO | WO 02/053557 | 7/2002 |
| WO | WO 2006/026395 | 3/2006 |
| WO | WO 2007/031933 | 3/2007 |

OTHER PUBLICATIONS

Gould, P.L., Salt selection for basic drugs, International Journal of Pharmaceutics, 1986, 33, pp. 201-217.
U.S. Appl. No. 12/388,142, filed Feb. 18, 2009, Adesuyi et al.
Neidhart, W., et al. "Discovery of RO 48/5695: A Potent Mixed Endothelin Receptor Optimized from Bosentan", Bioorganic & Medical Chemistry Letters, vol. 7, No. 17, pp. 2223-2228, 1997.
Gohring, W., et al., "Development of a Process to Prepare 2-Cyanopyrimidine on Commercial Scale", Chimia, vol. 50, pp. 538-543, Nov. 1996.
Nugent, R., et al., "Pyrimidine Thioethers: A Novel Class of HIV-1 Reverse Transcriptase Inhibitors with Ativity Against BHAP-Resistant HIV", J. Med. Chem., vol. 41, pp. 3793-3803, 1998.
March, J., "Advanced Organic Chemistry (Fourth Edition)", p. 449 and references cited therein, 1992.
Kohara, Y., et al., Synthesis and Angiotensin II Receptor Antagonistic Activities of Benzimidazole Derivatives Bearing Acidic Heterocycles as Novel Tetrazole Bioisosteres, J. Med. Chem. vol. 39, pp. 5228-5235, 1996.
Weiss, G., et al., Liebigs Ann. Chem., vol. 729, pp. 40-51, 1969.
Kloek, J., et al., An Improved Synthesis of Sulfamoyl Chlorides, J. Org. Chem., vol. 41, No. 25, pp. 4028-4029, 1976.
Dickinson, R., et al., "Thromboxane Modulating Agents. 3. IH-Imidazol-1-y[alkyl-and 3-Pyridinylalkyl-Substituted 3-[2-((Arylsulfonyl)amino)ethyl)benzenepropanoic Acid Derivatives as Dual Thromboxane Synthase Inhibitor/Thromboxane Receptor Antagonists", J. Med. Chem., vol. 40, pp. 3442-3452, 1997.
Cohen, E., et al., "Sulfamoyl Chloride, Sulfamides and Sulfimide", J. Am. Chem. Soc., vol. 84, pp. 1994-2002, 1962.

(Continued)

Primary Examiner — Sreeni Padmanabhan
Assistant Examiner — Kendra D Carter
(74) Attorney, Agent, or Firm — Hoxie & Associates LLC

(57) ABSTRACT

The invention relates to a product containing the compound of formula (I) below

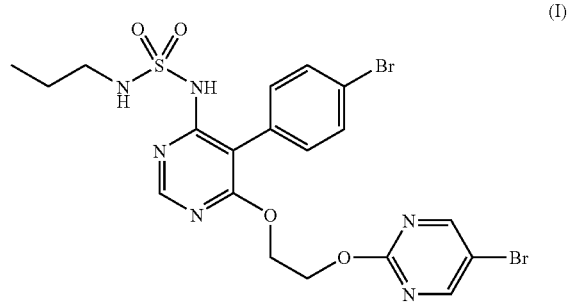

(I)

or a pharmaceutically acceptable salt of this compound, in combination with at least one compound having PDE5-inhibitory properties, or a pharmaceutically acceptable salt thereof, for therapeutic use, simultaneously, separately or over a period of time, in the treatment of a disease wherein vasoconstriction is involved.

11 Claims, No Drawings

OTHER PUBLICATIONS

Olson, R., et al., "Orally Active Isoxazoline Glycoprotein IIb/IIIa Antagonists with Extended Duration of Action", J. Med. Chem., vol. 42, pp. 1178-1192, 1999.

Crosby, D., et al., "n-Butyl 5-Chloro-2-pyrimidoxyacetate-A Plant Growth Regulator Analog", J.Org. Chem., vol. 25, pp. 1916-1919, Nov. 1960.

Morgan, E.D., "Synthesis of p-ALkylphenylacetic Acid", Tetrahedron, vol. 23, pp. 1735-1738, 1967.

Tozer, M., et al., "4-Chlorobenzyl Sulfonamide and Sulfamide Derivatives of Histamine Homologues: The Design of Potent Histamine H3 Receptor Antagonists", Bioorganic & Medicinal Chemistry Letter vol. 9, pp. 3103-3108, 1999.

Dewynter, G., et al., Tetrahedron, vol. 49, No. 1, pp. 65-76, 1993.

Rubanyi, G.M., et al., Endothelins: Molecular Biology, Biochemistry, Pharmacology, Physiology and Pathophysiology, Pharm. Reviews, vol. 46, No. 3, 1994.

Arai, H., et al., "Cloninc & Expression of a cDNA Encoding an Endothelin Receptor", Nature, vol. 348, pp. 730-732, 1990.

Breu, V., et al. "In vitro Characterization of Ro 48/2005, a Novel Synthetic Non-Peptide Endothelin Antagonist of Eta and ETb Receptors", FEBS 13244, vol. 334, No. 2, pp. 210-214, Nov. 1993.

Neidhart, W., et al., "The Discovery of Nonpeptide Endothelin Receptor Antagonists. Progression Towards Bosentan", Chimia, vol. 50, pp. 519-524, Nov. 1996.

McMillen, M., et al., "Endothelins: Polyfunctional Cytokines" J. Amer. College of Surgeons, vol. 180, pp. 621-640, 1995.

Ogawa, Y., et al., "Molecular Cloning of a Non-Isopeptide-Selective Human Endothelin Receptor", Biochem. Biophy. Research Comm. vol. 178, No. 1, pp. 248-255, Jul. 1991.

Ohlstein, E., et al., "Endothelin-1 Modulates Vascular Smooth Muscle Structure and Vasomotion; Implications in Cardiovascular Pathology" Drug Development Research, vol. 29, pp. 108-128, 1993.

Sakurai, T., et al., "Cloning of cDNA Encoding a Non-Isopeptide-Selective Subtype of the Endothelin Receptor" Nature, vol. 348, pp. 732-735, Dec. 1990.

Sumner, M., et al., "Endothelin Eta and ETb Receptors Mediate Vascular Smooth Muscle Contraction", Br.J. Pharmacol., vol. 107, pp. 858-860, 1992.

Yanagisawa, M., et al., "A Novel Potent Vasoconstrictor Peptide Produced by Vascular Endothelial Cells", Nature, vol. 332, pp. 411-415, Mar. 1988.

Bennett, J. Claude, et al., Textbook of Medicine vol. 1, 20$^{th}$ Edition, pp. 1004-1010, 1996.

Iglarz, M., et al., Pharmacology of Macitentan, an Orally Active Tissue-Targeting Dual Endothelin Receptor Antagonist, *The Journal of Pharmacology and Experimental Therapeutics*, vol. 327, No. 3, pp. 736-745, 2008.

THERAPEUTIC COMPOSITIONS COMPRISING A SPECIFIC ENDOTHELIN RECEPTOR ANTAGONIST AND A PDE5 INHIBITOR

CROSS REFERENCE TO RELATED APPLICATIONS

This application is a United States National Stage Application under 35 U.S.C. 371 of PCT Application No. PCT/IB2007/053448, filed on Aug. 28, 2007, which claims the benefit of PCT Application No. PCT/IB2006/052999, filed on Aug. 29, 2006, and PCT Application No. PCT/IB2006/053857, filed on Oct. 19, 2006, the contents of each of which are incorporated herein by reference in their entirety.

The present invention relates to a product containing the compound of formula (I) below

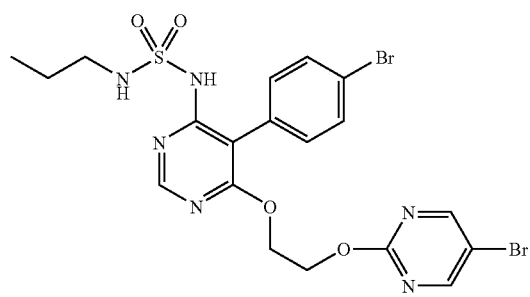

or a pharmaceutically acceptable salt of this compound, in combination with at least one compound having PDE5-inhibitory properties, or a pharmaceutically acceptable salt thereof, for therapeutic use, simultaneously, separately or over a period of time, in the treatment of a disease wherein vasoconstriction is involved.

PCT publication WO 02/053557 describes endothelin receptor antagonists including the compound of formula (I) and the use of said endothelin receptor antagonists in the treatment of various diseases wherein vasoconstriction is involved (i.a. heart failure, angina pectoris, pulmonary and systemic hypertension and erectile dysfunction).

PDE-5 inhibitors have been notably described in the following patent documents:
  U.S. Pat. No. 5,250,534 (describing pyrazolopyrimidinone derivatives as PDE-5 inhibitors and i.a. sildenafil as well as the use of the same for i.a. hypertension and heart failure) and EP 1097 711 (describing i.a. sildenafil for pulmonary hypertension);
  WO 99/24433 (describing i.a. vardenafil as well as the use of the same for i.a. hypertension, angina pectoris and erectile dysfunction);
  U.S. Pat. No. 5,859,006 (describing i.a. tadalafil as well as the use of the same for i.a. hypertension, pulmonary hypertension, angina and congestive heart failure);
  WO 00/27848 (describing i.a. udenafil and the use thereof for impotence).

The Applicant has now surprisingly found that the combination of the compound of formula (I) with a compound having PDE5-inhibitory properties results in an unexpected synergistic effect in the treatment of diseases wherein vasoconstriction is involved.

Therefore a subject of this invention is a product containing the compound of formula (I) as described before or a pharmaceutically acceptable salt of said compound of formula (I), in combination with at least one (and preferably one) compound having PDE5-inhibitory properties, or a pharmaceutically acceptable salt thereof, for therapeutic use, simultaneously, separately or over a period of time, in the treatment of a disease wherein vasoconstriction is involved.

The following paragraphs provide definitions of the various terms used in the present patent application and are intended to apply uniformly throughout the specification and claims, unless an otherwise expressly set out definition provides a broader or narrower definition.

"PDE-5" stands in the present application for cyclic guanosine 3', 5'-monophosphate (cGMP) phosphodiesterase type 5.

"Simultaneously" or "simultaneous", when referring to a therapeutic use, means in the present application that the therapeutic use concerned consists in the administration of two or more active ingredients by the same route and at the same time.

"Separately" or "separate", when referring to a therapeutic use, means in the present application that the therapeutic use concerned consists in the administration of two or more active ingredients at approximately the same time by at least two different routes.

By therapeutic administration "over a period of time" is meant in the present application the administration of two or more ingredients at different times, and in particular an administration method according to which the entire administration of one of the active ingredients is completed before the administration of the other or others begins. In this way it is possible to administer one of the active ingredients for several months before administering the other active ingredient or ingredients. In this case, no simultaneous administration occurs.

By "disease wherein vasoconstriction is involved" is meant in particular hypertension, pulmonary hypertension (including pulmonary arterial hypertension), diabetic arteriopathy, heart failure, erectile dysfunction or angina pectoris.

By "compound having PDE5-inhibitory properties" is meant a compound that, when submitted to the "Test for the determination of PDE5 $IC_{50}$" described in the present patent application, has an $IC_{50}$ equal or lower than 1 μM.

Specific examples of compounds having PDE5-inhibitory properties include the compounds having the following structures (names):

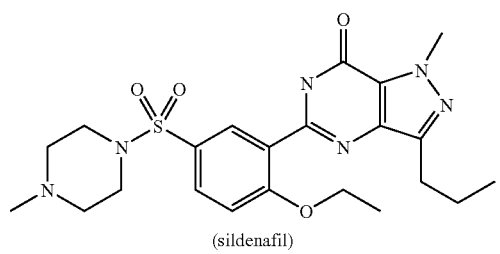
(sildenafil)

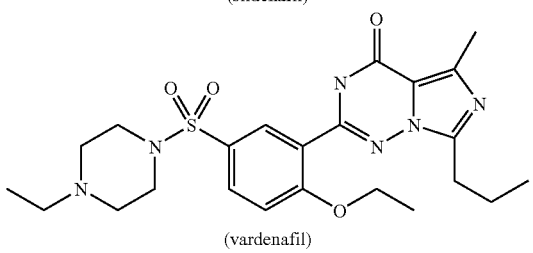
(vardenafil)

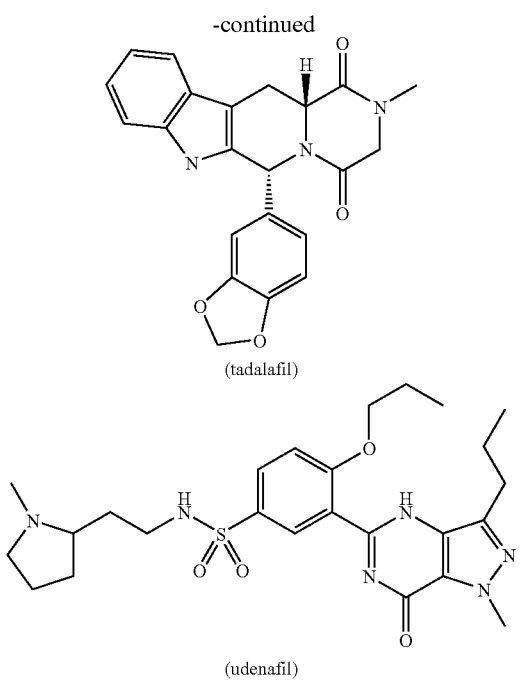

(tadalafil)

(udenafil)

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, any reference to a compound of formula (I) or to a compound having PDE5-inhibitory properties is to be understood as referring also to the pharmaceutically acceptable salts thereof, as appropriate and expedient.

Preferably, the product according to this invention will be such that the compound of formula (I) and the compound having PDE5-inhibitory properties are intended for a therapeutic use which takes place simultaneously or over a period of time.

According to one preferred variant of this invention, the compound of formula (I) and the compound having PDE5-inhibitory properties will be intended to be administered simultaneously.

According to another preferred variant of this invention, the compound of formula (I) and the compound having PDE5-inhibitory properties will be intended to be administered over a period of time.

The period of time intended for the therapeutic use of a product according to this invention will be at least one week, and preferably at least one or more months (for example six months). This period of time may also be the whole life of the patient that receives the product. Preferably, administration of compound of formula (I) will be alternated with administration of a compound having PDE5-inhibitory properties, and the interval between such administration will not exceed two or three days (and more preferably not exceed one day).

Preferably, the compound having PDE5-inhibitory properties will be selected from sildenafil, vardenafil, tadalafil and udenafil. More preferably, the compound having PDE5-inhibitory properties will be sildenafil or tadalafil.

According to one particularly preferred variant of the invention the compound having PDE5-inhibitory properties will be sildenafil.

According to another particularly preferred variant of the invention the compound having PDE5-inhibitory properties will be tadalafil.

The administration route of the compound of formula (I) and that of the compound having PDE5-inhibitory properties is preferably the same. In particular, the common administration route for the compound of formula (I) and for the compound having PDE5-inhibitory properties will be the intravenous or oral route (and notably the oral route).

Though the exact administration doses of a product according to this invention will have to be determined by the treating physician, it is expected that a dose of 0.05 to 2 mg (and preferably 0.1 to 1 mg) of compound of formula (I) per kg of patient body weight combined with a dose 0.01 to 1 mg (and preferably 0.05 to 0.5 mg) of tadalafil per kg of patient body weight, both compounds being intended to be administered by oral route, or combined with a dose 0.1 to 2 mg (and preferably 0.2 to 1 mg) of sildenafil per kg of patient body weight will be appropriate, both compounds being intended to be administered by oral route as well.

Preferably, the disease intended to be treated by a product according to this invention will be selected from hypertension, pulmonary hypertension, diabetic arteriopathy, heart failure, erectile dysfunction and angina pectoris. More preferably, the disease intended to be treated by a product according to this invention will be selected from hypertension and pulmonary hypertension. In particular, the disease intended to be treated by a product according to this invention will be pulmonary hypertension (and notably pulmonary arterial hypertension).

The invention also relates to a pharmaceutical composition containing, as active principles, the compound of formula (I) below

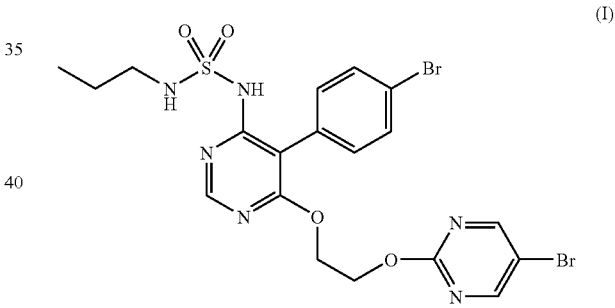

(I)

or a pharmaceutically acceptable salt of this compound, in combination with at least one (and preferably one) compound having PDE5-inhibitory properties, or a pharmaceutically acceptable salt thereof, as well as at least one excipient.

The invention further relates to the use of the compound of formula (I) below

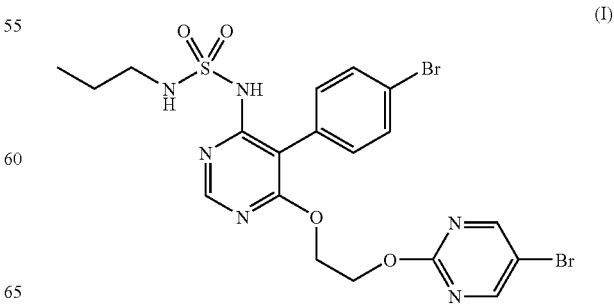

(I)

or a pharmaceutically acceptable salt of this compound, in combination with at least one (and preferably one) compound having PDE5-inhibitory properties, or a pharmaceutically acceptable salt thereof, for the manufacture of a medicament intended to treat a disease wherein vasodilation is required.

Besides, preferences indicated for the product according to this invention of course apply mutatis mutandis to the pharmaceutical compositions and uses of this invention.

Particular embodiments of the invention are described in the following Examples, which serve to illustrate the invention in more detail without limiting its scope in any way.

EXAMPLES

To illustrate the usefulness of this invention, the association of the compound of formula (I), administered orally at a dose of 0.3 mg/kg, with tadalafil, administered orally at a dose of 10 mg/kg, has been studied in two different hypertension models, namely the Dahl salt-sensitive rat model and the spontaneously hypertensive rat model. Furthermore, the association of the compound of formula (I), administered orally at a dose of 0.3 mg/kg, with sildenafil, administered orally at a dose of 30 mg/kg, has been studied in the spontaneously hypertensive rat model. The protocols used are detailed in the part entitled "Pharmacological properties of the invention compounds" hereafter.

Pharmacological Properties of the Invention Compounds

The experimental methods described hereafter can be used to show the pharmacological properties of the invention compounds.

Dahl Salt-Sensitive Rat Model

Dahl salt-sensitive (Dahl-S) were purchased from Harlan (Netherlands). The rats were housed by group during the acclimatization period and single-housed after implantation of the telemetry device. All animals were maintained under identical conditions and had free access to normal pelleted rat chow and water. Dahl salt-sensitive rats develop hypertension only upon exposure to salt intake. They were administered a high-salt (8%) chow diet (Purina series 5500). Five weeks after starting salt administration, a telemetry system was implanted under anaesthesia by inhalation of 2.5% isoflurane (in 70% $O_2$+30% $N_2O$). Under aseptic conditions, a pressure radio-frequency transmitter was implanted into the peritoneal cavity, and a sensing catheter was inserted in the descending aorta and advanced pointing upstream to slightly below the renal artery bifurcation. The transmitter was sutured to the abdominal musculature and the skin was closed. A receiver platform transformed the radio signal into digitized input, that was sent to a dedicated personal computer (Compaq, deskpro). Arterial blood pressure measurements were calibrated by using an input from an ambient pressure reference. Telemetry units were obtained from Data Sciences (St. Paul, Minn., USA).

The compounds were administered at least 2 weeks after telemetry system implantation. The compound of formula (I) and the compound having PDE5-inhibitory properties were prepared in 5% arabic gum and administered by oral gavage. The acute effects of the compound of formula (I), the compound having PDE5-inhibitory properties and their combination on blood pressure were measured by collecting data at 5-minute intervals up to 72 h after oral administration. Hourly means of blood pressure were calculated for each rat. Each rat served as its own control, by using the blood pressure data of the last 24 hours before drug administration. The two curves (blood pressure of the control period and blood pressure of the treatment period) were plotted together and the area between curves (ABC) from 0 to 72 hours was calculated. The higher the ABC, the stronger the effect of the item tested for lowering blood pressure.

Spontaneously Hypertensive Rat Model

The same protocol was used as for the Dahl salt-sensitive rat model, except that spontaneously hypertensive rats (SHR) replace the Dahl-S rats and that the SHR rats did not receive any salt diet. The SHR rats were purchased from Harlan (Netherlands).

Test for the Determination of PDE5 $IC_{50}$:

In order to estimate the extent of inhibition for PDE5 activity of a test compound, the following test is carried out. Phosphodiesterase-5 enzyme (PDE 5) is separated from human corpus cavernosal tissues. About 3 g of this tissue is homogenized with 12 ml of HEPES buffer (20 mM HEPES, 250 mM sucrose, 1 mM EDTA, 1 mM PMSF, pH 7.2) at 4° C. The solution is filtered with double-layered gauze and centrifuged (100.000×g) for 60 min at 4° C. The supernatant is filtered with 0.2 μm filter paper and separated by HPLC (Mono Q anion exchange column) with concentration gradient of 0-500 mM NaCl to elute PDE isozymes. The enzyme activity is measured on each column fraction by the following process to separate the PDE5 fraction and the PDE5 inhibition of the test compound is measured using the PDE5 fraction. To 1.5 ml tube are added 100 μl of reaction mixture (15 mM Tris-HCl, 5 mM $MgCl_2$, 0.5 mg/ml BSA, pH 7.4) and the appropriate amount of test compound fraction and test compound and the mixture is mixed well. To this solution is added $^3$H-cAMP or $^3$H-cGMP (500 nM, 2 μCi/ml), the mixture is reacted in the incubator of 30° C. for about 1 hour and the reaction is quenched by putting the tube into boiling water for about 45 seconds to 2 min. Then the tube is chilled in ice bath for about 5 min. To this tube is added snake venom (1 mg/ml, 100 μl) or 5-nucleotidase (0.1 unit/tube) and the mixture is reacted in an incubator at 37° C. for 10 min and chilled in an ice bath. 3 times volume of methanol to the resin is added to the anion exchange resin (Bio-Rad resin. AG 1-X2, 200-400 mesh) which has been already washed with 0.5N HCl, $H_2O$, 0.5N NaOH. $H_2O$. 0.5N MCI and $H_2O$ in order and adjusted to pH 5. Then 1 ml of the pretreated resin is dispensed into each tube with vortexing. The mixture is left at 4° C. for 15 min with occasional vortexing and centrifuged (10,000 rpm) for about 5 min to sediment the resin. The supernatant (700 μl) is transferred to a liquid scintillation vial, and mixed with 10 ml of scintillation cocktail. After stabilizing the solution by leaving it overnight, the radioactivity of the tube is measured by β-counter.

If the test compound has an $IC_{50}$ equal or lower than 1 μM, it is considered as having PDE5-inhibitory properties for the purpose of this patent application. If the test compound has an $IC_{50}$ higher than 1 μM, it is considered as not having PDE5-inhibitory properties for the purpose of this patent application.

Example 1

Following the test protocol described previously in the part entitled "Dahl salt-sensitive rat model", oral administration of the compound of formula (I) and tadalafil decreased blood pressure in Dahl-S rats: the compound of formula (I) (0.3 mg/kg) decreased blood pressure with an ABC of 256 and tadalafil (10 mg/kg) with an ABC of 310. The ABC after oral administration of the combination (compound of formula (I) at 0.3 mg/kg and tadalafil at 10 mg/kg) was 923, demonstrating a synergistic effect.

Example 2

Following the test protocol described previously in the part entitled "Spontaneously hypertensive rat model", oral administration of the compound of formula (I) and tadalafil decreased blood pressure in SHR rats: the compound of formula (I) (0.3 mg/kg) decreased blood pressure with an ABC of 44 and tadalafil (10 mg/kg) with an ABC of 286. The ABC after oral gavage of the combination (compound of formula (I) at 0.3 mg/kg and tadalafil at 10 mg/kg) was 444, confirming the synergistic effect.

Example 3

Following the test protocol described previously in the part entitled "Spontaneously hypertensive rat model", oral administration of the compound of formula (I) and sildenafil decreased blood pressure in SHR rats: the compound of formula (I) (0.3 mg/kg) decreased blood pressure with an ABC of 38 and sildenafil (30 mg/kg) with an ABC of 229. The ABC after oral gavage of the combination (compound of formula (I) at 0.3 mg/kg and sildenafil at 30 mg/kg) was 317, confirming the synergistic effect.

The invention claimed is:

1. A product containing the compound of formula (I) below

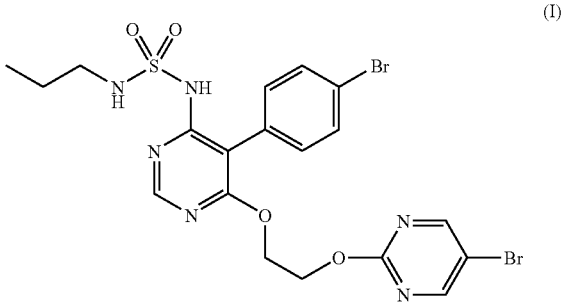

(I)

in free or pharmaceutically acceptable salt form, in combination with at least one compound having PDE5-inhibitory properties, in free or a pharmaceutically acceptable salt form, for therapeutic use, simultaneously, separately or over a period of time, in the treatment of a disease wherein vasoconstriction is involved.

2. The product according to claim 1, wherein the compound having PDE5-inhibitory properties is selected from sildenafil, vardenafil, tadalafil and udenafil.

3. The product according to claim 2, wherein the compound having PDE5-inhibitory properties is tadalafil.

4. The product according to claim 2, wherein the compound having PDE5-inhibitory properties is sildenafil.

5. The product according to claim 1, wherein the disease wherein vasoconstriction is involved is selected from hypertension, pulmonary hypertension, diabetic arteriopathy, heart failure, erectile dysfunction and angina pectoris.

6. A pharmaceutical composition containing, as active principles, the compound of formula (I) as described in claim 1, in free or pharmaceutically acceptable salt form, in combination with at least one compound having PDE5-inhibitory properties, in free or pharmaceutically acceptable salt form, as well as at least one excipient.

7. The pharmaceutical composition according to claim 6, wherein the compound having PDE5-inhibitory properties is selected from sildenafil, vardenafil, tadalafil and udenafil.

8. The pharmaceutical composition according to claim 7, wherein the compound having PDE5-inhibitory properties is tadalafil.

9. The pharmaceutical composition according to claim 7, wherein the compound having PDE5-inhibitory properties is sildenafil.

10. A method for the treatment of hypertension or pulmonary hypertension comprising administering to a patient in need thereof an effective amount of a compound of formula (I) as described in claim 1, in free or pharmaceutically acceptable salt form, in combination with at least one compound having PDE5-inhibitory properties, in free or pharmaceutically acceptable salt form.

11. The method according to claim 10, wherein the compound having PDE5-inhibitory properties is selected from sildenafil, vardenafil, tadalafil and udenafil.

* * * * *